(12) United States Patent
Tunheim et al.

(10) Patent No.: US 9,228,918 B2
(45) Date of Patent: Jan. 5, 2016

(54) SYSTEMS AND METHODS FOR INSPECTING AND MONITORING A PIPELINE

(71) Applicant: Halliburton Energy Services, Inc., Houston, TX (US)

(72) Inventors: Ola Tunheim, Bryne Rogaland (GB); Robert P. Freese, Pittsboro, NC (US); Laurence James Abney, Sandnes Rogaland (NO); Christopher M. Jones, Houston, TX (US); James Robert MacLennan, Aberdeen Grampian (GB)

(73) Assignee: Halliburton Energy Services, Inc., Houston, TX (US)

( * ) Notice: Subject to any disclaimer, the term of this patent is extended or adjusted under 35 U.S.C. 154(b) by 101 days.

(21) Appl. No.: 14/282,022

(22) Filed: May 20, 2014

(65) Prior Publication Data
US 2014/0252251 A1    Sep. 11, 2014

Related U.S. Application Data

(62) Division of application No. 13/617,625, filed on Sep. 14, 2012, now Pat. No. 8,765,061.

(51) Int. Cl.
*G01N 21/00* (2006.01)
*G01M 3/38* (2006.01)
*G01N 21/85* (2006.01)
*G01N 21/31* (2006.01)
*G01N 21/954* (2006.01)
*G01N 21/17* (2006.01)
*G01N 21/27* (2006.01)
(Continued)

(52) U.S. Cl.
CPC ............ *G01M 3/38* (2013.01); *G01M 3/005* (2013.01); *G01N 21/17* (2013.01); *G01N 21/27* (2013.01); *G01N 21/31* (2013.01); *G01N 21/85* (2013.01); *G01N 21/954* (2013.01); *G01J 3/02* (2013.01)

(58) Field of Classification Search
None
See application file for complete search history.

(56) References Cited

U.S. PATENT DOCUMENTS

| | | | |
|---|---|---|---|
| 6,198,531 B1 | 3/2001 | Myrick et al. | |
| 6,529,276 B1 | 3/2003 | Myrick | |
| 6,809,821 B2 | 10/2004 | Thomasson et al. | |

(Continued)

OTHER PUBLICATIONS

Official Action for New Zealand Patent Application No. 704080 dated Jul. 6, 2015.

(Continued)

*Primary Examiner* — Robert Xu
(74) *Attorney, Agent, or Firm* — McDermott Will & Emery LLP; Scott Brown

(57) ABSTRACT

An example method includes introducing a movable inline inspection device into a pipeline, the movable inline inspection device having a housing that defines a conduit therein which provides fluid communication through the movable inline inspection device in the form of a bypass fluid, the conduit having one or more optical computing devices arranged thereon for monitoring the bypass fluid, wherein each optical computing device has at least one integrated computational element arranged therein, generating an output signal corresponding to a characteristic of the bypass fluid with at least one detector arranged within each optical computing device, receiving the output signal from each optical computing device with a signal processor communicably coupled to the at least one detector of each optical computing device, and determining with the signal processor the characteristic of the bypass fluid detected by each optical computing device.

20 Claims, 3 Drawing Sheets

(51) Int. Cl.
*G01M 3/00* (2006.01)
*G01J 3/02* (2006.01)

(56) References Cited

U.S. PATENT DOCUMENTS

| | | |
|---|---|---|
| 6,931,149 B2 | 8/2005 | Hagene et al. |
| 7,123,844 B2 | 10/2006 | Myrick |
| 7,697,141 B2 | 4/2010 | Jones et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 8,049,881 B2 | 11/2011 | Myrick et al. |
| 8,208,147 B2 | 6/2012 | Myrick et al. |
| 8,358,418 B2 | 1/2013 | Myrick et al. |
| 8,765,061 B2 | 7/2014 | Tunheim et al. |
| 2006/0142955 A1 | 6/2006 | Jones et al. |
| 2009/0140133 A1 | 6/2009 | Abney |
| 2009/0182693 A1 | 7/2009 | Fulton et al. |
| 2009/0219538 A1 | 9/2009 | Myrick et al. |
| 2009/0219539 A1 | 9/2009 | Myrick et al. |
| 2010/0149523 A1 | 6/2010 | Heideman et al. |
| 2010/0315638 A1 | 12/2010 | Goohs et al. |
| 2012/0038354 A1 | 2/2012 | Gies |
| 2013/0284895 A1 | 10/2013 | Freese et al. |
| 2013/0284897 A1 | 10/2013 | Freese et al. |
| 2013/0284898 A1 | 10/2013 | Freese et al. |
| 2013/0284904 A1 | 10/2013 | Freese et al. |
| 2013/0286399 A1 | 10/2013 | Freese et al. |
| 2014/0080172 A1 | 3/2014 | Tunheim et al. |

OTHER PUBLICATIONS

International Search Report and Written Opinion for PCT/US2013/058709 dated Dec. 6, 2013.

SYSTEMS AND METHODS FOR INSPECTING AND MONITORING A PIPELINE

BACKGROUND

The present invention relates to optical analysis systems and, in particular, systems and methods that employ optical analysis systems to inspect and monitor the internals of a pipeline.

In the oil and gas industry, a tool known as a "pig" refers to any of a variety of movable inline inspection devices that are introduced into and conveyed (e.g., pumped, pushed, pulled, self-propelled, etc.) through a pipeline or a flow line. Pigs often serve various basic functions while traversing the pipeline, including cleaning the pipeline to ensure unobstructed fluid flow and separating different fluids flowing through the pipeline. Modern pigs, however, can be highly sophisticated instruments that include electronics and sensors employed to collect various forms of data during the trip through the pipeline. Such pigs, often referred to as smart pigs or inline inspection pigs, can be configured to inspect the internals or interior of the pipeline, and capture and record specific geometric information relating to the sizing and positioning of the pipeline at any given point along the length thereof. Smart pigs can also be configured to determine pipe wall thickness and pipe joint weld integrity with the appropriate sensing equipment.

Smart pigs, which are also referred to as inline inspection tools, typically use technologies such as magnetic flux leakage (MFL) and electromagnetic acoustic transducers to detect surface pitting, corrosion, cracks, and weld defects in steel/ferrous pipelines. Acoustic resonance technology and ultrasonics have also been employed to detect various aspects and defects of a pipeline. After a pigging run has been completed, positional data recorded from various external sensors is combined with the pipeline evaluation data (corrosion, cracks, etc.) derived from the pig to generate a location-specific defect map and characterization. The combined data is useful in determining the general location, type, and size of various types of pipe defects. The data can also be used to judge the severity of the defects and help repair crews locate and repair the defects.

While conventional smart pigs are generally able to locate various pipeline defects, they are, for the most part, unable to provide adequate reasons as to why the particular defect is occurring or has occurred. For instance, pipeline corrosion can develop for a myriad of reasons, including the presence of acids or other caustic substances and chemicals flowing within the pipeline. Knowing "why" the corrosion or other event is occurring, may prove advantageous to an operator in stopping or otherwise reversing the corrosive effects.

Also, conventional smart pigs are largely unable to efficiently monitor the formation of both organic and inorganic deposits detected in pipelines and flow lines. Typically, the analysis of such deposits is conducted off-line using laboratory analyses, such as spectroscopic and/or wet chemical methods, which analyze an extracted sample of the fluid. Although off-line, retrospective analyses can be satisfactory in certain cases, but they nonetheless do not allow real-time or near real-time analysis capabilities but instead often require hours to days to complete the analysis. During the lag time between collection and analysis, the characteristics of the extracted sample of the chemical composition oftentimes changes, thereby making the properties of the sample non-indicative of the true chemical composition or characteristic. Efficiently and accurately identifying organic and inorganic deposits in pipelines could prove advantageous to pipeline operators in mitigating costly corrective action. Moreover, accurately identifying the concentration of such deposit buildups in pipelines may provide valuable information on the effectiveness of treatments designed to counteract the deposits.

SUMMARY OF THE INVENTION

The present invention relates to optical analysis systems and, in particular, systems and methods that employ optical analysis systems to inspect and monitor the internals of a pipeline.

In one aspect of the disclosure, a system for monitoring a pipeline is disclosed. The system may include a movable inline inspection device arranged within the pipeline and having a housing that defines a conduit therein, the conduit providing fluid communication through the movable inline inspection device, one or more optical computing devices arranged on the conduit for monitoring a bypass fluid flowing through the conduit, the one or more optical computing devices comprising, at least one integrated computational element configured to optically interact with the bypass fluid and thereby generate optically interacted light, and at least one detector arranged to receive the optically interacted light and generate an output signal corresponding to a characteristic of the bypass fluid. The system may also include a signal processor communicably coupled to the at least one detector of each optical computing device for receiving the output signal of each optical computing device, the signal processor being configured to determine the characteristic of the fluid as detected by each optical computing device and provide a resulting output signal indicative of the characteristic of the bypass fluid.

In another aspect of the disclosure, a method of monitoring a pipeline is disclosed. The method may include introducing a movable inline inspection device into the pipeline, the movable inline inspection device having a housing that defines a conduit therein which provides fluid communication through the movable inline inspection device in the form of a bypass fluid, the conduit having one or more optical computing devices arranged thereon for monitoring the bypass fluid, wherein each optical computing device has at least one integrated computational element arranged therein, generating an output signal corresponding to a characteristic of the bypass fluid with at least one detector arranged within each optical computing device, receiving the output signal from each optical computing device with a signal processor communicably coupled to the at least one detector of each optical computing device, and determining with the signal processor the characteristic of the bypass fluid detected by each optical computing device.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
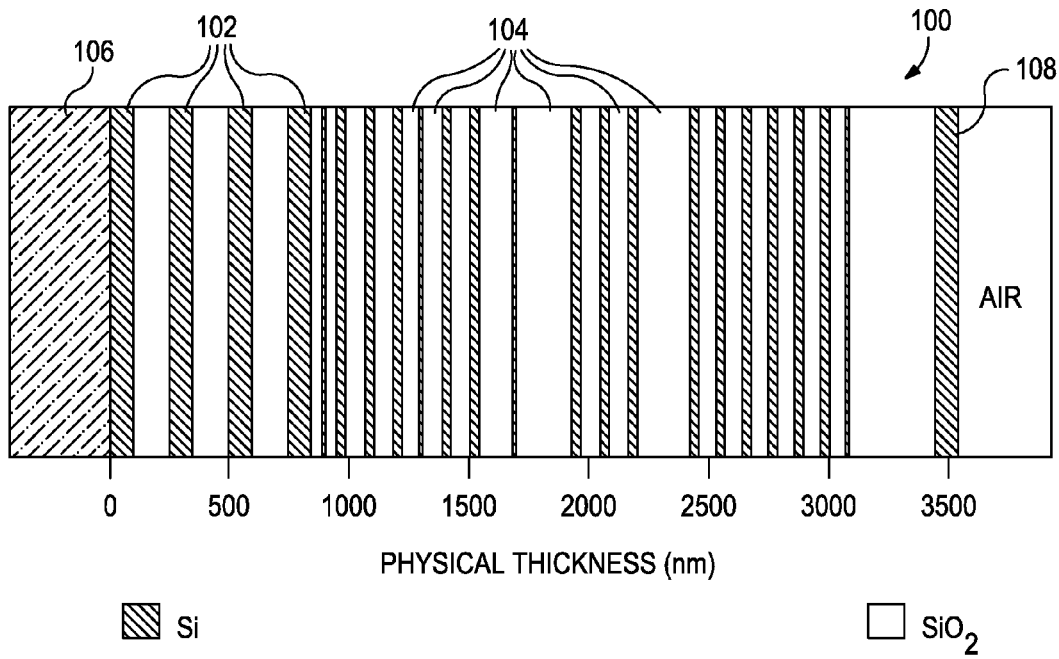
FIG. 1 illustrates an exemplary integrated computation element, according to one or more embodiments.

The present invention relates to optical analysis systems and, in particular, to systems and methods that employ optical analysis systems to inspect and monitor the internals of a pipeline.

The exemplary systems and methods described herein employ various configurations of optical computing devices, also commonly referred to as "opticoanalytical devices," for the inspection and monitoring of the internals of a pipeline, including the inner radial surface of the pipeline and the fluid flowing therein. The optical computing devices may be arranged or otherwise installed on a movable inline inspection device, also known as a "pig". A significant and distinct advantage of the disclosed optical computing devices, which are described in more detail below, is that they can be configured to specifically detect and/or measure a particular component or characteristic of interest of a chemical composition or other substance, thereby allowing qualitative and/or quantitative analyses of pipeline substances to occur without having to extract a sample and undertake time-consuming analyses of the sample at an off-site laboratory. As a result, the optical computing devices can advantageously provide real-time or near real-time monitoring of the pipeline internals that cannot presently be achieved with either onsite analyses at a job site or via more detailed analyses that take place in a laboratory.

In operation, for example, the optical computing devices as installed on a movable inline inspection device may be useful and otherwise advantageous in scanning and chemically mapping the internals of a pipeline wall and also monitoring the fluids flowing within the pipeline. In other aspects the optical computing devices as installed on the movable inline inspection device may further be useful and otherwise advantageous in monitoring chemical reactions occurring within the pipeline, monitoring the effectiveness of a maintenance operation conducted within the pipeline, detecting substances at all points around and flowing through the movable inline inspection device, determining the speed and distance of the movable inline inspection device within the pipeline, detecting pipeline welds and their chemical compositions, inspecting the internal coating(s) of the pipeline, detecting corrosion and/or the severity of metal loss in the pipeline, combinations thereof, and many other applications as will be appreciated by those skilled in the art. With the ability to undertake real-time or near real-time chemical composition analyses, the disclosed systems and methods may provide some measure of proactive or responsive control over a fluid flow within the pipeline or a maintenance operation being undertaken therein. The systems and methods may further inform a pipeline owner or operator as to the exact location and cause of a pipeline defect, enable the collection and archival of fluid information in conjunction with operational information to optimize subsequent operations, and/or enhance the capacity for remote job execution.

Those skilled in the art will readily appreciate that the disclosed systems and methods may be suitable for use in the oil and gas industry since the described optical computing devices provide a cost-effective, rugged, and accurate means for inspecting and monitoring the internals of a pipeline used to convey or otherwise transport hydrocarbons. It will be appreciated, however, that the systems and methods described herein are equally applicable to other technology fields including, but not limited to, the food industry, the medicinal and drug industry, various industrial applications, heavy machinery industries, mining industries, or any field where it may be advantageous to inspect and monitor in real-time or near real-time the internals of a pipeline, tubes or other type of flow line. For example, installing the disclosed optical computing devices on a movable inline inspection device may prove useful in inspecting and monitoring the internals of potable water lines or sewer lines and related piping structures.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water, such as seawater, fresh water, potable water, drinking water, or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a subterranean formation fluid. Fluids can also include various flowable mixtures of solids, liquids and/or gases. Illustrative gases that can be considered fluids, according to the present embodiments, include, for example, air, nitrogen, carbon dioxide, argon, helium, methane, ethane, butane, and other hydrocarbon gases, combinations thereof, and/or the like.

As used herein, the term "characteristic" refers to a chemical, mechanical, or physical property of a substance or material. A characteristic of a substance may include a quantitative value or a concentration of one or more chemical components present within the substance. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or a sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether the detector analyzes reflected or transmitted electromagnetic radiation may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or any other substance.

As used herein, the term "substance," or variations thereof, refers to at least a portion of a matter or material of interest to be evaluated using the described optical computing devices described herein as installed or otherwise arranged on a movable inline inspection device. In some embodiments, the substance is the characteristic of interest, as defined above, and may include any integral component of a pipeline or a fluid flowing within the pipeline, but may equally refer to any solid material or chemical composition. For example, the substance may include compounds containing elements such as barium, calcium, manganese, sulfur, sulfates, iron, strontium, chlorine, mercury, etc., and any other chemical composition that can lead to precipitation within a pipeline. The substance may also refer to paraffins (e.g., low molecular weight (M) n-alkanes ($C_{20}$-$C_{40}$) to high proportion of high M iso-alkanes), waxes, asphaltenes, aromatics, saturates foams, salts, dissolved mineral salts (i.e., associated with produced brines and scaling potential), particulates, sand or other solid particles, etc., and any other chemical composition that can lead to the formation of deposits within a pipeline. In some aspects, the substance refers to welds within a pipeline, or bacteria that tends to congregate in such welds. In yet other aspects, the substance may refer to pipeline coatings and the pipeline material itself.

In other aspects, the substance may include any material or chemical composition added to the pipeline in order to treat the pipeline for hydrates or the build up of one or more organic or inorganic deposits. Exemplary treatment substances may include, but are not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be referred to as a substance as well.

As used herein, the term "sample," or variations thereof, refers to at least a portion of a substance or chemical composition of interest to be tested or otherwise evaluated using the described optical computing device(s) as installed or otherwise arranged on a movable inline inspection device. The sample includes the characteristic of interest, as defined above, and may be any fluid, as defined herein, or otherwise any solid substance or material such as, but not limited to, welds or the inner wall of a pipeline.

As used herein, the term "pipeline" includes any conduit in which a fluid is moved, including any onshore or offshore flow system, such as mainline systems, risers, flow lines used to transport untreated fluid between a wellhead and a processing facility, and flow lines used to transport hydrocarbon products. It should be understood that the use of the term "pipeline" is not necessarily limited to hydrocarbon pipelines unless otherwise denoted or required by a specific embodiment.

The exemplary systems and methods described herein will include at least one optical computing device used for near or real-time inspection and monitoring of the internals of a pipeline, and in particular one or more chemical compositions or substances present within the pipeline. The optical computing device may include an electromagnetic radiation source, at least one processing element (e.g., integrated computational elements), and at least one detector arranged to receive optically interacted light from the at least one processing element. As disclosed below, however, in some embodiments the electromagnetic radiation source may be omitted from the optical computing device and instead the electromagnetic radiation may be derived from the chemical composition or substance being monitored. In some embodiments, the exemplary optical computing devices may be specifically configured for detecting, analyzing, and quantitatively measuring a particular characteristic or analyte of interest of the chemical composition or substance. In other embodiments, the optical computing devices may be general purpose optical devices, with post-acquisition processing (e.g., through computer means) being used to specifically detect the characteristic of interest.

In some embodiments, suitable structural components for the exemplary optical computing devices are described in commonly owned U.S. Pat. Nos. 6,198,531; 6,529,276; 7,123,844; 7,834,999; 7,911,605; 7,920,258; and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample extraction and processing. In this regard, the optical computing devices can be specifically configured to detect and analyze particular characteristics and/or analytes of interest of a chemical composition, such as a substance present within a pipeline or disposed on the surface of the pipeline. As a result, interfering signals are discriminated from those of interest in the substance by appropriate configuration of the optical computing devices, such that the optical computing devices provide a rapid response regarding the characteristic(s) of interest based on the detected output. In some embodiments, the detected output can be converted into a voltage that is distinctive of the magnitude or concentration of the characteristic being monitored. The foregoing advantages and others make the described optical computing devices particularly well suited for hydrocarbon processing and downhole use, but may equally be applied to several other technologies or industries, without departing from the scope of the disclosure.

The optical computing devices arranged on or otherwise coupled to the movable inline inspection device can be configured to detect not only the composition and concentrations of a sample fluid or substance found within a pipeline, but they also can be configured to determine physical properties and other characteristics of the sample fluid or substance as well, based on an analysis of the electromagnetic radiation received therefrom. For example, the optical computing devices can be configured to determine the concentration of an analyte and correlate the determined concentration to a characteristic of a substance by using suitable processing means. As will be appreciated, the optical computing devices may be configured to detect as many substances or as many characteristics or analytes of the substance as desired. All that is required to accomplish the monitoring of multiple characteristics is the incorporation of suitable processing and detection means within the optical computing device for each substance of interest. In some embodiments, the properties of the substance can be a combination of the properties of the analytes detected therein (e.g., a linear, non-linear, logarithmic, and/or exponential combination). Accordingly, the more characteristics and analytes that are detected and analyzed using the optical computing devices, the more accurately the properties of the given substance will be determined.

The optical computing devices described herein utilize electromagnetic radiation to perform calculations, as opposed to the hardwired circuits of conventional electronic processors. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The optical computing devices described herein are capable of extracting the information of the spectral fingerprint of multiple characteristics or analytes, and converting that information into a detectable output regarding the overall properties of the substance. That is, through suitable configurations of the optical computing devices, electromagnetic radiation associated with a characteristic or analyte of interest of a substance can be separated from electromagnetic radiation associated with all other components of the substance in order to estimate the properties of the substance in real-time or near real-time.

As stated above, the processing elements used in the exemplary optical computing devices described herein may be characterized as integrated computational elements (ICE). Each ICE is capable of distinguishing electromagnetic radiation related to a characteristic of interest corresponding to a substance from electromagnetic radiation related to other components of the substance. Referring to FIG. 1, illustrated is an exemplary ICE 100 suitable for use in the optical computing devices that may be coupled to or otherwise attached to a movable inline inspection device. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the substance being monitored.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
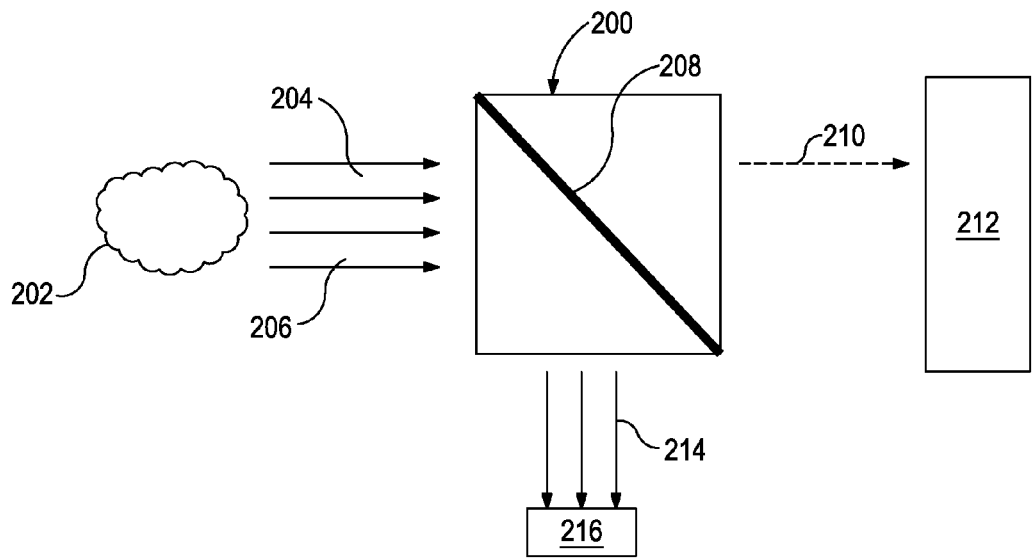
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a substance 202 produces an output of electromagnetic radiation (e.g., sample-interacted light), some of which is electromagnetic radiation 204 corresponding to the characteristic of interest and some of which is background electromagnetic radiation 206 corresponding to other components or characteristics of the substance 202. In some embodiments, the substance 202 may be a fluid, but in other embodiments may be a solid material, as defined herein.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source (if present), which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605; 7,920,258; 8,049,881 and U.S. patent application Ser. No. 12/094,460 (U.S. Pat. App. Pub. No. 2009/0219538); Ser. No. 12/094,465 (U.S. Pat. App. Pub. No. 2009/0219539); and Ser. No. 13/456,467, incorporated herein by reference, as indicated above.

The beams of electromagnetic radiation 204, 206 impinge upon an exemplary ICE 208 arranged within the optical computing device 200. The ICE 208 may be similar to the ICE 100 of FIG. 1, and therefore will not be described again in detail. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to a characteristic of interest in the substance 202, may be conveyed to a detector 212 for analysis and quantification. In some embodiments, the detector 212 is configured to produce an output signal in the form of a voltage that corresponds to the particular characteristic of interest in the substance 202. In at least one embodiment, the signal produced by the detector 212 and the concentration of the characteristic of interest may be directly proportional. In other embodiments, the relationship may be a polynomial function, an exponential function, and/or a logarithmic function. The reflected optically interacted light 214, which may be related to characteristics of other components and chemical compositions of the substance 202, can be directed away from detector 212. In alternative configurations, the ICE 208 may be configured such that the reflected optically interacted light 214 can be related to the characteristic of interest, and the transmitted optically interacted light 210 can be related to other chemical compositions and/or components of the substance 202.

In some embodiments, a second detector 216 can be included in the optical computing device 200 and arranged to detect the reflected optically interacted light 214. In other embodiments, the second detector 216 may be arranged to detect the electromagnetic radiation 204, 206 derived from the substance 202 or electromagnetic radiation directed toward or before the substance 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to or otherwise being detected by the second detector 212.

The characteristic(s) of interest being analyzed using the optical computing device 200 can be further processed computationally to provide additional characterization information about the substance 202. In some embodiments, the identification and concentration of each analyte of interest in the substance 202 can be used to predict certain physical characteristics of the substance 202. For example, the bulk characteristics of the substance 202 can be estimated by using a combination of the properties conferred to the substance 202 by each analyte.

In some embodiments, the concentration or magnitude of the characteristic of interest determined using the optical computing device 200 can be fed into an algorithm operating under computer control. The algorithm may be configured to make predictions on how the characteristics of the substance 202 would change if the concentrations of the characteristic of interest are changed relative to one another. In some embodiments, the algorithm can produce an output that is readable by an operator for consideration. For example, based on the output, the operator may want to undertake some remedial action to remedy, reduce, or otherwise prevent the future detection of a monitored substance. In other embodiments, the algorithm can be programmed to take proactive process control by automatically initiating a remedial effort when a predetermined toxicity or impurity level of the substance is reported or otherwise detected.

The algorithm can be part of an artificial neural network configured to use the concentration of each characteristic of interest in order to evaluate the overall characteristic(s) of the substance 202 and thereby determine when a predetermined toxicity or impurity level has been reached or otherwise surpassed. Illustrative but non-limiting artificial neural networks are described in commonly owned U.S. patent application Ser. No. 11/986,763 (U.S. Patent App. Pub. No. 2009/0182693), which is incorporated herein by reference. It is to be recognized that an artificial neural network can be trained using samples of predetermined characteristics of interest having known concentrations, compositions, and/or properties, and thereby generating a virtual library. As the virtual library available to the artificial neural network becomes larger, the neural network can become more capable of accurately predicting the characteristic of interest corresponding to a sample fluid or other substance having any number of analytes present therein. Furthermore, with sufficient training, the artificial neural network can more accurately predict the characteristics of the sample fluid or substance, even in the presence of unknown substances.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site but able to access the job site via wireless communication.

Referring now to FIGS. 3A-3D, illustrated are various embodiments of an exemplary system 300 for inspecting and monitoring the internals of a pipeline 302. Specifically, the system 300 may be used to detect a characteristic of a substance found or otherwise present within the pipeline 302. In some embodiments, the substance may be located on the pipeline 302 itself, such as on an inner radial surface 304 thereof, and may include, but is not limited to, wall coatings, organic and/or inorganic deposits, iron oxides, sulfates, chlorides, surface deposition bacteria (i.e., aerobic and sulfur-reducing bacteria), sulfates, wax deposition, asphaltenes, plated lead, water, brines, combinations thereof, and the like. In other embodiments, the substance may be present in the fluid 306 flowing within the pipeline 302 such as, but not limited to, a particular chemical composition, a hazardous substance, a contaminant, hydrates, a chemical reaction, radium (i.e., for gas applications), corrosive or corrosion compounds, corrosion inhibitors, various tags that may assist to identify or illuminate compounds of interest, combinations thereof, and the like.

The system 300 may include a movable inline inspection device 308 as arranged within the pipeline 302. In some embodiments, the movable inline inspection device 308 may be a pipeline "pig," as known in the art. In other embodiments, however, the movable inline inspection device 308 may be any inspection mechanism capable of being pumped or otherwise moved through a pipeline 302 for the purpose of inspecting and monitoring the internals of the pipeline 302, including the fluid 306 therein. In at least one embodiment, for example the inline inspection device 308 may be a tethered device that is pulled through the pipeline 302 or a section of the pipeline 302. In other embodiments, the movable inline inspection device 308 may be self-propelled or may be a foam "pig," without departing from the scope of the disclosure. The particular type and design of movable inline inspection device 308 to be used may depend on several factors such as the type and volume of the fluid 306 within the pipeline 304 and the specific purpose of using the movable inline inspection device 308.

As depicted, the movable inline inspection device 308 may have a generally cylindrical housing 310. In other embodiments, the housing 310 may have a square cross-section or any other geometric shape, without departing from the scope of the disclosure. One or more drive discs 312 may be coupled to or otherwise arranged at each end of the housing 310. In other embodiments, the drive discs 312 may also be known as or referred to as piston seals, seal elements, or seal discs, as recognized by those skilled in the art. The drive discs 312 may be generally circular, having an outer circumference or periphery configured to form a close or interference fit with the inner radial surface 304 of the pipeline 302.

In one or more embodiments, the drive discs 312 may be formed of polyurethane, but may also be made of nylon, polyoxymethylene (POM, i.e., DELRIN®), polytetrafluoroethylene (PTFE, i.e., TEFLON®), elastomers (e.g., rubber) combinations thereof, or the like. The drive discs 312 may be flexible and compressible, so that they are able to form an essentially fluid tight seal with the inner radial surface 304 of the pipeline 302, but will simultaneously be configured to flex so that the movable inline inspection device 308 may be moved through the pipeline 302 without excessive frictional resistance. In some embodiments, the drive discs 312 may also provide a cleaning function by mechanically removing contaminants or other deposits formed on the inner radial 304 surface of the pipeline 302 as the movable inline inspection device 308 moves therethrough. In yet other embodiments, the drive discs 312 may be designed not to fully seal the pipeline 302, but may be configured to allow fluid to bypass the inline inspection device 308, without departing from the scope of the disclosure.

Those skilled in the art will readily recognize that while two drive discs 312 are depicted at each end of the housing 310, the actual number of drive discs 312 in any given embodiment may be more or less than two, depending on the particular application of the system 300 and design constraints of the movable inline inspection device 308. For example, the number of drive discs 312 may be selected to achieve a desired amount of sealing engagement with the inner radial surface 304 of the pipeline 302. Accordingly, while the drive discs 312 are depicted in the figures as having a generally circular shape, each may equally exhibit any other geometrical shape configured to restrict the flow of fluids between the movable inline inspection device 308 and the pipeline 302, and nonetheless achieve substantially the same results. It will be readily appreciated by those skilled in the art that various design modifications and alterations to the movable inline inspection device 308 may be had, without departing from the scope of the disclosure.

Figure 3A:
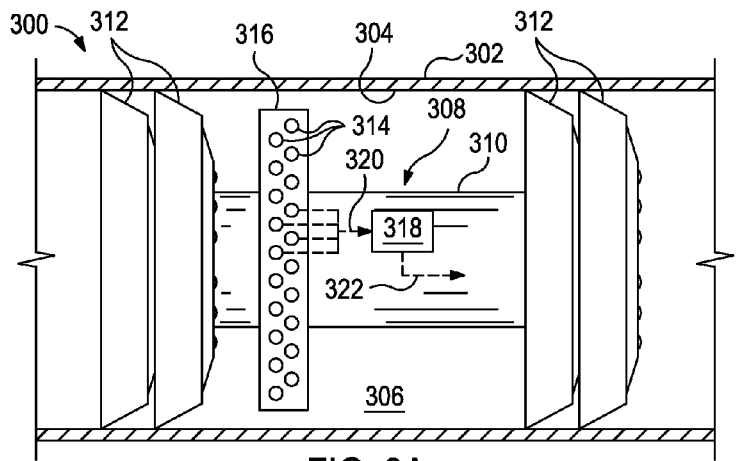
FIGS. 3A-3D illustrate exemplary systems for monitoring the internals of a pipeline, according to one or more embodiments.

The system 300 may further include one or more optical computing devices 314 configured to detect and determine a characteristic of the substance being monitored. Referring specifically to FIG. 3A, for example, the one or more optical computing devices 314 may be seated in or otherwise form an integral part of a sensor housing 316 coupled to the movable inline inspection device 308. In some embodiments, the sensor housing 316 may be a radial disc attached to or otherwise extending radially from the outer radial surface of the housing 310. In other embodiments, however, the sensor housing 316 may be any other rigid member or structure capable of receiving and securing the optical computing devices 314 therein.

As illustrated, the one or more optical computing devices 314 are seated within the sensor housing 316 such that they are arranged about the outer periphery of the sensor housing 316 and therefore in close proximity to the inner radial surface 304 of the pipeline 302. As a result, as the movable inline inspection device 308 advances through the pipeline 302, the one or more optical computing devices 314 may be configured to continuously monitor and/or inspect the inner radial surface 304 of the pipeline 302 at generally every radial angle. Those skilled in the art will readily appreciate the advantages this may provide in scanning or mapping the inner radial surface 304 for chemical compositions or other defects.

In some embodiments, the one or more optical computing devices 314 may be similar to the optical computing device 200 of FIG. 2, and therefore may be best understood with reference thereto. It should be noted that, while several optical computing devices 314 are shown in FIG. 3A, the system 300 may employ any number of optical computing devices 314, without departing from the scope of the disclosure. Indeed, the specific number of optical computing devices 314 used in any given application may depend primarily on design constraints of the movable inline inspection device 308 and the relative spacing between adjacent optical computing devices 314 as seated in the sensor housing 316. Moreover, each device 314 may be housed and sealed within the sensor housing 316 or otherwise within individual casings configured to substantially protect the internal components of the respective devices 314 from damage or contamination from the external environment. Accordingly, the devices 314 may be generally protected from contaminants, pressure, and temperature that may be experienced or otherwise encountered within the pipeline 302.

In operation, each device 314 may be configured to receive and detect optically interacted radiation derived from a substance present within the pipeline 302, such as substances located on the inner radial surface 304 of the pipeline 302. In at least one embodiment, the one or more optical computing devices 314 may be configured to provide an initial impulse of electromagnetic radiation to the substance from an electromagnetic radiation source (not shown). This impulse of electromagnetic radiation optically interacts with the substance and generates the optically interacted radiation that is detectable by the devices 314. Once optically interacted radiation is detected, each device 314 may be configured to generate an output signal 320 that corresponds to a particular characteristic of interest as detected in the substance. In some embodiments, each optical computing device 314 may be configured to detect a different characteristic of interest. In other embodiments, each optical computing device 314 may be configured to detect the same characteristic of interest.

In yet other embodiments, one or more sets of optical computing devices 314 may be strategically arranged about the sensor housing 316 at predetermined locations and configured to detect a particular characteristic of a substance, while other sets of optical computing devices 314 may be strategically arranged about the sensor housing 316 at other predetermined locations and configured to detect other characteristics of the substance or a characteristic of another substance altogether. For instance, the pipeline 302 may be divided into radial quadrants or other radial divisions and each radial quadrant or division may be monitored for specific substances found therein or likely to be found therein. As a result, every radial angle of the pipeline 302 may be intelligently monitored using the optical computing devices 314.

In at least one embodiment, for example, a gas bubble (e.g., methane) may be present at about the twelve o'clock position, while an oil/water mixture may be present at about the three and nine o'clock positions and water may be present at about the six o'clock position. Accordingly, a first set of optical computing devices 314 may be arranged to monitor a first radial division of the inner radial surface 304 of the pipeline 302 and detect a characteristic of a first substance, which may be the gas bubble or the water/oil mixture. Likewise, a second set of optical computing devices 314 may be arranged to monitor a second radial division of the inner radial surface 304 of the pipeline 302 and detect a characteristic of a second substance, which may be the water or the water/oil mixture. As will be appreciated, the first and second substances may be the same or different, and the characteristics of each substance detected by each device 314 may also be either the same or different. As a result, the optical computing devices 314 may be strategically arranged about the inner radial surface 304 at predetermined radial angles in order to intelligently monitor the substance(s) found in each radial quadrant or division of the pipeline 302.

Those skilled in the art will readily appreciate the several advantages that are provided to an operator by strategically arranging the devices 314 about varying radial positions in the sensor housing 316. For example, this may allow the operator to chemically map every radial angle of the inner radial surface 304 of the pipeline 302 and thereby intelligently inform the operator of the real-time or near real-time conditions found at each radial angle therein. Moreover, since the movable inline inspection device 308 is advanced through the pipeline 302 during operation, this valuable information can be simultaneously obtained for axial sections of the entire length of the pipeline 302, or specific portions thereof, thereby informing the operator of which substances are present within each length of the pipeline 302, at what particular radial angle such substances are detects, and what their respective concentrations are.

Such information may help an operator to intelligently initiate remedial efforts designed to counteract defects in the pipeline 302 at specifically identified points along the pipeline 302. Such information may further help an operator to strategically remove unwanted chemical compositions from the pipeline 302 and otherwise strategically maintain the pipeline 302 in proper working order, including the removal/replacement of damaged or affected parts or sections. Moreover, such information may help shed light on the nature of the occurrence, i.e., how the corrosion/defect occurred, such as by a dent in the original pipeline 302, a flow issue, a pipe design defect or weakness, etc. As will be appreciated, the ability to chemically map the inner radial surface 308 of the pipeline 302 provides diagnostic data as to why the pipeline 302 may be experiencing metal loss. For instance, the metal loss could be due to lack of corrosion inhibitor chemicals at one particular point in the pipeline 302 or it could be due to bacteria activity.

In some embodiments, the one or more optical computing devices 314 may be communicably coupled to a signal processor 318, also included in the system 300 or otherwise forming part thereof. Each device 314 may be configured to convey its respective output signal 320 to the signal processor 318 for processing or storage. For instance, the signal processor 318 may be a computer including a non-transitory machine-readable medium and configured to process the output signals and thereby provide a resulting output signal 322 indicative of the detected characteristic(s) of interest. In some embodiments, the signal processor 318 may be programmed with an algorithm configured to process the incoming output signals 320 and provide, for example, a chemical map of the pipeline 302. In other embodiments, the signal processor 318 may include an on-board memory or storage device configured to store the data received from each optical computing device 314. The stored data may be characterized as the resulting output signal 322 and subsequently downloaded at a predetermined time for processing.

The signal processor 318 may be communicably coupled to one or more communication interfaces (not shown) and otherwise configured to convey the resulting output signal 322, either wired or wirelessly, to an external processing device (not shown) for consideration by an operator or for further processing and manipulation. In some embodiments, for example, one communication interface may be a communication port (compatible with Ethernet, USB, etc.) defined or otherwise provided on the housing 310 or any other portion of the movable inline inspection device 308. The communication port may allow the signal processor 318 to be coupled to an external processing device, such as a computer, a hard drive, a handheld computer, a personal digital assistant (PDA), or other wireless transmission device. Once coupled thereto, the signal processor 318 may be able to download its stored data (e.g., data related to the characteristic(s) of interest).

In other embodiments, the communication interface may be a wireless transmitter or link (not shown) arranged within the housing 310. The signal processor 318 may be communicably coupled to the wireless link which may operate in accordance with any known wireless technology (e.g., Bluetooth, Wi-Fi, acoustic, etc.) and therefore be configured to wirelessly telecommunicate with any remote wireless device such as, but not limited to, radios, cellular telephones, PDAs, wireless networks, satellite telecommunications, and the like. Accordingly, the signal processor 318 may be configured to wirelessly transmit the resulting output signal 322 to the operator for consideration. In other embodiments, the signal processor 318 may be configured to trigger one or more remedial actions when a predetermined threshold of a concentration of a particular characteristic has been breached or otherwise surpassed. Such triggering actions can include, for example, remotely opening a valve to mix batches at a preprogrammed point, adding a substance to the pipeline 302, reducing the influx of the substance into the pipeline 302, etc.

Figure 3B:
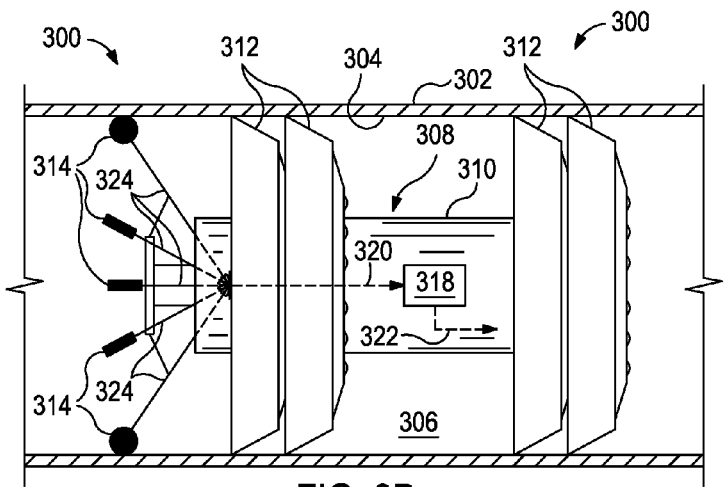

Referring now to FIG. 3B, with continued reference to FIG. 3A, illustrated is another embodiment of the system 300 exhibiting an alternative arrangement or configuration of the optical computing devices 314 for inspecting and monitoring the internals of a pipeline 302. In some embodiments, the system 300 of FIG. 3B may include a plurality of fingers 324 extending from the housing 310 and configured to situate the one or more optical computing devices 314 adjacent the inner radial surface 304 of the pipeline 302. Specifically, the fingers 324 may provide a corresponding rigid support structure for each optical computing device 314 and may thereby arrange the devices 314 such that they face the inner radial surface 304 for monitoring substances found thereon.

While the fingers 324 are depicted as extending from the housing 310, or a portion thereof, the fingers 324 may equally extend from any other portion of the movable inline inspection device 308, without departing from the scope of the disclosure, and obtain substantially the same results. Moreover, as with prior embodiments, while only five optical computing devices 314 are depicted in FIG. 3B, it will be appreciated that any number of devices 314 with corresponding fingers 324 or rigid support structures may be employed.

As with the system 300 of FIG. 3A, in operation, each device 314 may be configured to receive and detect optically interacted radiation derived from a substance present within the pipeline 302, including substances found on the inner radial surface of the pipeline 302. Once optically interacted radiation is detected, each device 314 may be configured to generate a corresponding output signal 320 corresponding to a particular characteristic of interest as detected in the substance, and convey the same to the signal processor 318 for processing. As with prior embodiments, each optical computing device 314 may be configured to detect the same or a different characteristic of interest. In other embodiments, the fingers 324 may be configured to arrange one or more sets of optical computing devices 314 at predetermined radial angles within the pipeline 302 such that the devices 314 are able to detect particular characteristics of one or more substances at specific radial angles within the pipeline 302. Accordingly, the fingers 324 may strategically arrange the optical computing devices 314 in order to intelligently monitor the substance(s) found at predetermined radial angles in the pipeline 302, thereby providing a user with a chemical map of the internals of the pipeline 302 as the movable inline inspection device 308 advances therein.

Figure 3C:
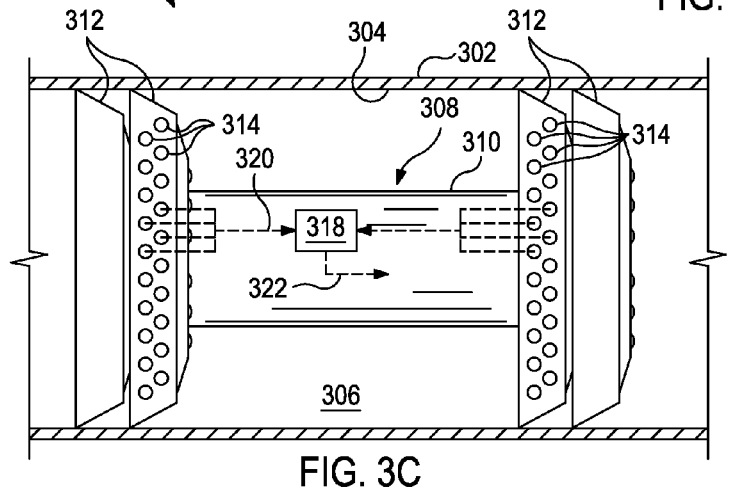

Referring now to FIG. 3C, with continued reference to FIGS. 3A and 3B, illustrated is another embodiment of the system 300 exhibiting an alternative arrangement or configuration of the optical computing devices 314 for inspecting and monitoring the internals of a pipeline 302. Specifically, the one or more optical computing devices 314 may be arranged on or otherwise housed in one or more of the drive discs 312. In at least one embodiment, the optical computing devices 314 may be molded into the drive discs 312 and thereby secured thereto for monitoring the inner radial surface 304 of the pipeline 302. While FIG. 3C depicts the optical computing devices 314 as being arranged on two drive discs 312, it will be appreciated that the devices 314 may be arranged on only one drive disc 312 or more than two drive discs 312, without departing from the scope of the disclosure. Those skilled in the art will readily recognize that an increased number of optical computing devices 314 arranged on additional drive discs 312 may increase the scanning and mapping capabilities of the movable inline inspection device 308, such that more substances can be monitored, more characteristics of interest in each substance can be detected, and higher resolutions can be acquired.

As illustrated, the one or more optical computing devices 314 are arranged about the outer periphery of the one or more drive discs 312 and therefore in close proximity to the inner radial surface 304 of the pipeline 302. As a result, as the movable inline inspection device 308 advances through the pipeline 302, the one or more optical computing devices 314 may be configured to continuously monitor and/or inspect the inner radial surface 304 of the pipeline 302 at generally every radial angle.

As with the systems 300 of FIGS. 3A and 3B, in operation, each device 314 may be configured to receive and detect optically interacted radiation derived from a substance present within the pipeline 302. Once optically interacted radiation is detected, each device 314 may be configured to generate a corresponding output signal 320 corresponding to a particular characteristic of interest as detected in the substance, and convey the same to the signal processor 318 for processing. As with prior embodiments, each optical computing device 314 may be configured to detect the same or a different characteristic of interest. In other embodiments, one or more sets of optical computing devices 314 may be strategically arranged about the corresponding drive disc 312 at predetermined locations and configured to detect a particular characteristic of a substance at predetermined radial angles within the pipeline 302, while other sets of optical computing devices 314 may be strategically arranged about the corresponding drive disc 312 at other predetermined locations and configured to detect other characteristics of the substance or a characteristic of another substance altogether at predetermined radial angles. Accordingly, the optical computing devices 314 may be strategically arranged to intelligently monitor the substance(s) found at predetermined radial angles in the pipeline 302, thereby providing a user with a chemical map of the internals of the pipeline 302 as the movable inline inspection device 308 advances therethrough.

Those skilled in the art will readily appreciate the various and numerous applications that the systems 300 of FIGS. 3A-3C, and alternative configurations thereof, may be suitably used with. For example, the system 300 may be used to determine the velocity of the movable inline inspection device 308 as it travels within the pipeline 302. In some embodiments, the velocity of the movable inline inspection device 308 may be determined using two axially-spaced optical computing devices 314, each being arranged on the movable inline inspection device 308 at a known distance from each other. Each device 314 may be configured to measure or detect a known feature of the pipeline 302, such as a weld or a coupling. The output signal 320 from each device 314 may correspond to a detection of the known feature of the pipeline 302, and the signal processor 318 may be configured to compute the velocity of the inline inspection device 308 by computationally combining the output signals 320 from each device 314, which may entail determining the difference between detection times of each device 314. In other embodiments, the axially-spaced devices 314 may be configured as an imaging device capable of analyzing how the image has been skewed from frame to frame to determine the velocity.

In other embodiments, the systems 300 of FIGS. 3A-3C may be used to detect welds on the inner radial surface 304 of the pipeline 302, or points where lengths of pipe segments are joined together to form the pipeline 302. In at least one embodiment, one or more of the optical computing devices 314 may be configured to detect a chemical composition used in the flux employed to generate the weld in the pipeline 302. In other embodiments, the one or more optical computing devices 314 may be configured to detect a known reacted substance that will typically be found around or otherwise form part of a weld. In yet other embodiments, the one or more optical computing devices 314 may be configured to detect known bacteria that has a tendency to congregate in welds. In yet further embodiments, the one or more optical computing devices 314 may be configured to detect differing metal compositions in the pipeline 302, which would be indicative of the presence of a weld. The detected welds can, for instance, be used to correlate gathered data with drawings, etc. In at least one embodiment, by using a known length of each pipe segment over time, the detected welds may also be used to calculate the velocity of the movable inline inspection device 308 from the logged data.

Moreover, since the optical computing devices 314 are arranged to monitor the entire inner radial surface 304 of the pipeline 302, the systems 300 of FIGS. 3A-3C may be employed to inspect the integrity of the welds in the pipeline 302. For example, in some embodiments, detection of a weld, such as through the exemplary processes described above, may be configured to trigger another system or mechanism adapted to photograph or otherwise record an image of the weld. In at least one embodiment, the recorded image may be stored in a memory associated with the signal processor 315 and subsequently conveyed to the operator for consideration. In one or more other embodiments, the system 300 may be programmed to record an image of a weld, as described above, and then pass a predetermined number of subsequent welds before triggering the system or mechanism once again to record an image of a subsequent weld. As a result, an operator will be provided with a sampling inspection report of the welds along the length of the pipeline 302.

In some embodiments, the systems 300 of FIGS. 3A-3C may further be used to inspect an internal coating applied to the inner radial surface 304 of the pipeline 302. The internal coating may be made of, for example, polyurethane or polyvinylchloride, but may be other types of coatings known in the art, without departing from the scope of the disclosure. In operation, the one or more optical computing devices 314 may be configured to detect the chemical composition of the internal coating as the movable inline inspection device 308 moves through the pipeline 302. Locations where the internal coating is not detected by the optical computing devices 314 may be indicative of where the internal coating has been worn off, for example, or where the pipeline 302 has otherwise been damaged or is absent. Accordingly, the systems 300 may be configured to provide an operator with an internal coating map of the pipeline 302 indicating locations where the internal coating has been compromised and, therefore, corrosion or metal loss may eventually result.

In some embodiments, the systems 300 of FIGS. 3A-3C may further be used to detect material stresses and/or dislocation in the inner radial surface 304 of the pipeline 302. For instance, the movable inline inspection device 308 may further include a gyro (not shown), an accelerometer (not shown), and a distance measurement system, such as those described herein, cooperatively configured to generate a better picture of the pipeline situation. A material stress measurement device could also be useful for other fields of inspection and monitoring.

In some embodiments, the systems 300 of FIGS. 3A-3C may further be used to detect metal loss in the inner radial surface 304 of the pipeline 302. For example, one or more of the optical computing devices may be configured to detect chemical compositions indicative of metal loss such as, but not limited to, iron oxides, rust, etc. Detection of such substances may correlate to the deterioration of the inner radial surface 304 of the pipeline 302 and may indicate locations where the pipeline 302 is compromised and otherwise weakened, which could eventually result in bursting of the pipeline 302. In other applications, one or more of the optical computing devices 314 may be combined with a focus mechanism (not shown), such as an auto-focus mechanism commonly found on commercially-available cameras. Adjustment of the focal point on the auto-focus mechanism may be indicative of a loss of metal at that particular location, and the degree to which the auto-focus mechanism is altered may be indicative of the exact depth or severity of the metal loss into the inner radial surface 304 of the pipeline 302. In such embodiments, a quadrant detector (not shown) may be useful in determining the exact distance the metal loss has corroded the inner radial surface 304 of the pipeline 302. In other embodiments, however, other detectors, such as split detectors or detector arrays may be used, without departing from the scope of the disclosure.

Figure 3D:
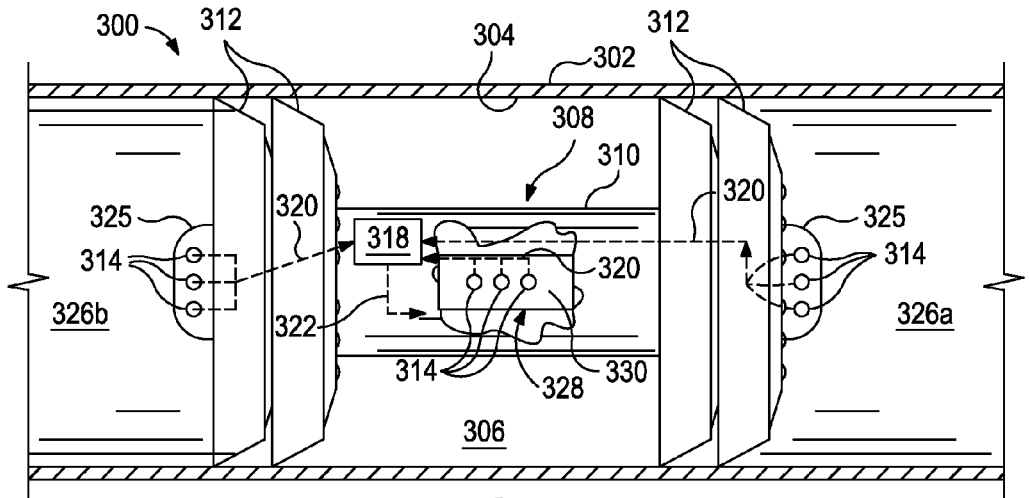

Referring now to FIG. 3D, with continued reference to FIGS. 3A-3C, illustrated is another embodiment of the system 300 exhibiting an alternative arrangement or configuration of the optical computing devices 314 for inspecting and monitoring the internals of a pipeline 302, and especially for monitoring the fluid 306 within the pipeline 302. Specifically, in at least one embodiment, one or more optical computing devices 314 may be arranged or otherwise disposed on one or both ends of the housing 310 of the movable inline inspection device 308. The optical computing devices 314 arranged at the front (i.e., to the right in FIG. 3D) may be configured to monitor the fluid 326a preceding the movable inline inspection device 308 and the optical computing devices 314 arranged at the back (i.e., to the left in FIG. 3D) may be configured to monitor the fluid 326b following the movable inline inspection device 308.

Some or all of the devices 314 arranged at either end of the movable inline inspection device 308 may be arranged within a housing 325 or similar casing structure configured to protect the devices 314 from external contamination or damage. The housing 325 may further be configured to generally protect the optical computing devices 314 from extreme pressures and/or temperatures that may be experienced or otherwise encountered within the pipeline 302.

Each of the optical computing devices 314 arranged on either end of the movable inline inspection device 308 may be configured to detect a characteristic of the fluid 326a,b before and after the movable inline inspection device 308, respectively. This may prove advantageous in applications where the fluid 306 within the pipeline 302 is a multiphase fluid, and the movable inline inspection device 308 may be used to, for example, separate fluid phases such that the fluid 326a before the movable inline inspection device 308 is different than the fluid 326b behind the movable inline inspection device 308. Moreover, the optical computing devices 314 may be useful as a quality control to monitor the state of different substances found in each fluid 326a,b. For instance, the system 300 of FIG. 3D may be used to monitor a leak of a transported batch over the movable inline inspection device 308, or the saturation of a reactive substance within the fluid 306, 326a,b. By logging such levels, the operator may be provided with valuable information on how effective the operation undertaken in the pipeline 302 was.

Moreover, having optical computing devices 314 arranged at either end of the movable inline inspection device 308 may prove useful since the device 308 itself may create a distortion in measurement where the device 308 compresses or "piles up" the material in front of the device 308, thereby creating a differential between the front and back of the device 308. As a result, an optical computing device 314 in just the front or just the back may not yield a representative result. Also, if there is a pressure differential between the front and back, then gases (e.g., hydrocarbons) may come out of solution and a differential measurement between the optical computing devices 314 arranged at either end could provide insight on potential bubble points, etc.

In other embodiments, the system 300 may include one or more optical computing devices 314 arranged on or within a conduit 328 disposed within the housing 310. In at least one embodiment, the conduit 328 may be configured to allow a bypass fluid 330 to pass through the movable inline inspection device 308, thereby fluidly communicating the fluid 326a in front of the movable inline inspection device 308 with the fluid 326b behind the movable inline inspection device 308. The optical computing devices 314 arranged on the conduit 328 may be configured to monitor the bypass fluid 330 for one or more characteristics found therein.

Those skilled in the art will readily appreciate the various and numerous applications that the system 300 of FIG. 3D, and alternative configurations thereof, may be suitably used with. For example, in one or more embodiments, the output signals 320 of any of the optical computing devices 314 may be indicative of a concentration of a substance, such as a corrosion or scale inhibitor, flowing within the fluid 306, 326a,b, or 330. In other embodiments, the output signals 320 of any of the optical computing devices 314 may be indicative of a concentration of one or more chemicals or chemical compositions flowing within the fluid 306, 326a,b, or 330. The chemical composition, for example, may be paraffin or calcium carbonate which tend to precipitate under certain conditions and form scale on the inner radial surface 304 of the pipeline 302. In yet other embodiments, the output signals 320 of any of the optical computing devices 314 may be indicative of other characteristics of the fluid 306, 326a,b, and/or 330, such as, but not limited to, pH, viscosity, density or specific gravity, and ionic strength, as measured at the first and second monitoring locations, respectively.

In some embodiments, the resulting output signal 322 of the system 300 of FIG. 3D may correspond to a characteristic of the fluid 306, 326a,b, and/or 330, where the characteristic is a concentration of a reagent or resulting product present in the fluid 306, 326a,b, and/or 330. Exemplary reagents found within the fluid 306, 326a,b, and/or 330 may include such compounds containing elements such as barium, calcium, manganese, sulfur, iron, strontium, chlorine, etc, and any other chemical substance that can lead to precipitation within a flow path. The reagent may also refer to paraffins waxes, asphaltenes, aromatics, saturates foams, salts, particulates, sand or other solid particles, combinations thereof, and the like. In other aspects, the reagent may include any substance added to the fluid 306, 326a,b, and/or 330 in order to cause a chemical reaction configured to treat the fluid 306, 326a,b, and/or 330 or the pipeline 302. Exemplary treatment reagents may include, but are not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like.

The reagent may be added to the fluid 306, 326a,b, and/or 330 to, for example, dissolve wax or asphaltene build-up, reduce a microbiological growth, etc. In other embodiments, the reagent may be a corrosion or scale inhibitor. In operation, the optical computing devices 314 may be configured to determine and report the concentration of the reagent in near or real-time, thereby ascertaining whether the reagent is working properly. For example, the optical computing devices 314 may be configured to determine when the reagent becomes fully saturated or reacted at some point, thereby indicating that the full potential of the reagent has been exhausted. In other embodiments, the optical computing devices 314 may be configured to determine the concentration of unreacted reagents, thereby indicating the efficacy of an operation. This may prove advantageous in being able to more accurately determine the optimal amounts of treatment reagents to provide for a specific operation.

In other embodiments, the resulting output signal 322 corresponds to a product, or the concentration thereof, that results from a chemical reaction process between two or more reagents within the fluid 306, 326a,b, and/or 330. In some embodiments, the characteristic of interest corresponding to the product may be indicative of, but not limited to, pH, viscosity, density or specific gravity, temperature, and ionic strength of a chemical compound. In at least one aspect, the bypass fluid 330 may carry information related to the real-time condition of the fluids within the pipeline 302, including the progress of any chemical reactions occurring therein or a determination of the effectiveness of a maintenance operation undertaken in the pipeline 302. By monitoring the chemical processes and their respective progression, the operator is able to determine how effective the maintenance operation within the pipeline 302 has been or whether additional maintenance operations should be undertaken. Additional description and discussion regarding optical computing devices configured to measure chemical reactions can be found in co-pending U.S. patent application Ser. No. 13/615,882, entitled "Systems and Methods for Monitoring Chemical Processes," the contents of which are hereby incorporated by reference to the extent not inconsistent with the present disclosure.

As with the systems 300 of FIGS. 3A-3C, in operation, each device 314 in FIG. 3D may be configured to receive and detect optically interacted radiation derived from the fluids (i.e., fluids 306, 326a,b, and/or 330) in the pipeline 302. Once optically interacted radiation is detected, each device 314 may be configured to generate a corresponding output signal 320 corresponding to a particular characteristic of interest as detected in the fluid, and convey the same to the signal processor 318 for processing. As with prior embodiments, each optical computing device 314 may be configured to detect the same or a different characteristic of interest. The resulting output signal 322 may then be provided to the operator at a predetermined time, or otherwise as described above.

Figure 4:
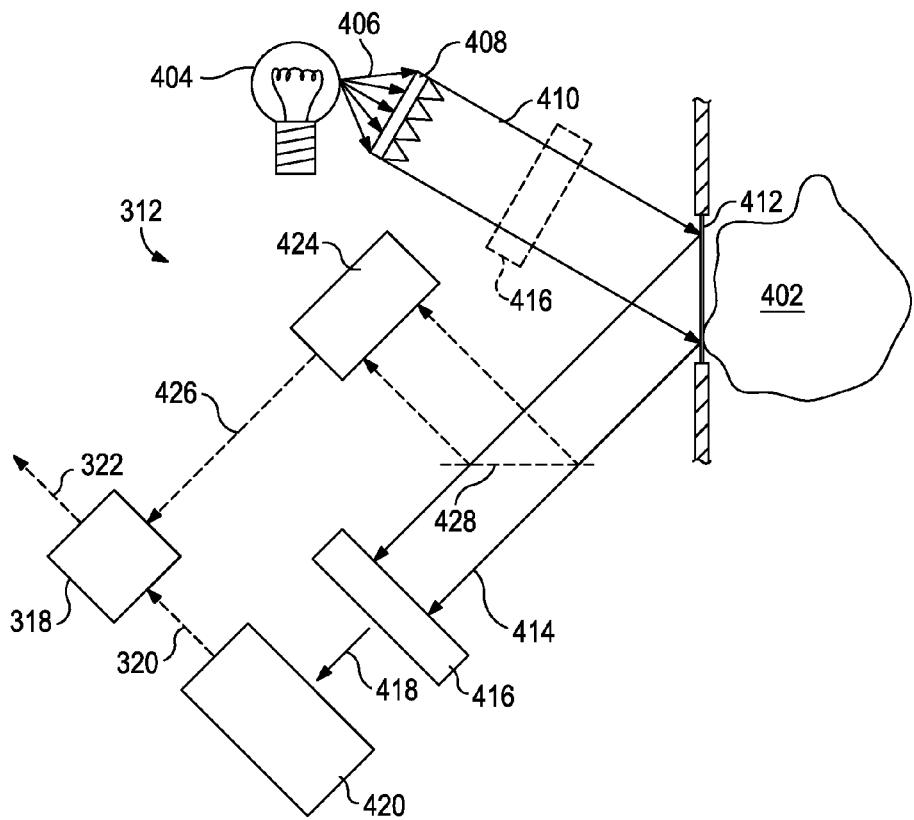
FIG. 4 illustrates an exemplary optical computing device, according to one or more embodiments.

Referring now to FIG. 4, with continued reference to FIGS. 3A-3D, illustrated is an exemplary schematic view of an optical computing device 314, according to one or more embodiments. As briefly discussed above, in operation, each optical computing device 314 may be configured to determine a particular characteristic of interest in a substance 402 found within or otherwise present in the pipeline 302 (FIGS. 3A-3D). Again, the substance 402 may be located on the pipeline 302 itself, such as a deposit or other defect found on an inner radial surface 304 thereof, or the substance 402 may be present in the fluid 306, 326a,b, 330 (FIG. 3D) flowing within the pipeline 302.

As illustrated, the optical computing device 314 may be housed within a casing or housing 403. In some embodiments, the housing 403 may be a portion of the sensor housing 316 of FIG. 3A, the drive discs 312 of FIG. 3C, or the housing 325 or conduit 328 of FIG. 3D. In other embodiments, however, the housing 403 may be distinct from each of the sensor housing 316, the drive discs 312, the housing 325, and/or the conduit 328 and otherwise configured to substantially protect the internal components of the device 314 from damage or contamination from the substance 402 or other external contaminants.

In one or more embodiments, the device 314 may include an electromagnetic radiation source 404 configured to emit or otherwise generate electromagnetic radiation 406. The electromagnetic radiation source 404 may be any device capable of emitting or generating electromagnetic radiation, as defined herein. For example, the electromagnetic radiation source 404 may be a light bulb, a light emitting diode (LED), a laser, a blackbody, a photonic crystal, an X-Ray source, combinations thereof, or the like. In some embodiments, a lens 408 may be configured to collect or otherwise receive the electromagnetic radiation 406 and direct a beam 410 of electromagnetic radiation 406 toward a location for detecting the substance 402. The lens 408 may be any type of optical device configured to transmit or otherwise convey the electromagnetic radiation 406 as desired. For example, the lens 408 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 408 may be omitted from the device 314 and the electromagnetic radiation 406 may instead be directed toward the substance 402 directly from the electromagnetic radiation source 404.

In one or more embodiments, the device 314 may also include a sampling window 412. The sampling window 412 may provide a transmission location for the beam 410 of electromagnetic radiation 406 to optically interact with the substance 402. The sampling window 412 may be made from a variety of transparent, rigid or semi-rigid materials that are configured to allow transmission of the electromagnetic radiation 406 therethrough. For example, the sampling window 412 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 412, the system 300 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 412, the electromagnetic radiation 406 impinges upon and optically interacts with the substance 402. As a result, optically interacted radiation 414 is generated by and reflected from the substance 402. Those skilled in the art, however, will readily recognize that alternative variations of the device 314 may allow the optically interacted radiation 414 to be generated by being transmitted, scattered, diffracted, absorbed, emitted, or re-radiated by and/or from the substance 402, without departing from the scope of the disclosure.

The optically interacted radiation 414 generated by the interaction with the substance 402 may be directed to or otherwise be received by an ICE 416 arranged within the device 314. The ICE 416 may be a spectral component substantially similar to the ICE 100 described above with reference to FIG. 1. Accordingly, in operation the ICE 416 may be configured to receive the optically interacted radiation 414 and produce modified electromagnetic radiation 418 corresponding to a particular characteristic of interest of the substance 402. In particular, the modified electromagnetic radiation 418 is electromagnetic radiation that has optically interacted with the ICE 416, whereby an approximate mimicking of the regression vector corresponding to the characteristic of interest in the substance 402 is obtained.

It should be noted that, while FIG. 4 depicts the ICE 416 as receiving reflected electromagnetic radiation from the substance 402, the ICE 416 may be arranged at any point along the optical train of the device 314, without departing from the scope of the disclosure. For example, in one or more embodiments, the ICE 416 (as shown in dashed) may be arranged within the optical train prior to the sampling window 412 and equally obtain substantially the same results. In other embodiments, the sampling window 412 may serve a dual purpose as both a transmission window and the ICE 416 (i.e., a spectral component). In yet other embodiments, the ICE 416 may generate the modified electromagnetic radiation 418 through reflection, instead of transmission therethrough.

Moreover, while only one ICE 416 is shown in the device 314, embodiments are contemplated herein which include the use of two or more ICE components in the device 314, each being configured to cooperatively determine the characteristic of interest in the substance 402. For example, two or more ICE components may be arranged in series or parallel within the device 314 and configured to receive the optically interacted radiation 414 and thereby enhance sensitivities and detector limits of the device 314. In other embodiments, two or more ICE components may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest of the substance 402. In other embodiments, the two or more ICE components may be configured to be positively or negatively correlated with the characteristic of interest of the sample. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

The modified electromagnetic radiation 418 generated by the ICE 416 may subsequently be conveyed to a detector 420 for quantification of the signal. The detector 420 may be any device capable of detecting electromagnetic radiation, and may be generally characterized as an optical transducer. In some embodiments, the detector 420 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 420 may be configured to produce the output signal 320 in real-time or near real-time in the form of a voltage (or current) that corresponds to the particular characteristic of interest in the substance 402. The voltage returned by the detector 420 is essentially the dot product of the optical interaction of the optically interacted radiation 414 with the respective ICE 416 as a function of the concentration of the characteristic of interest of the substance 402. As such, the output signal 320 produced by the detector 420 and the concentration of the characteristic of interest in the substance 402 may be related, for example, directly proportional. In other embodiments, however, the relationship may correspond to a polynomial function, an exponential function, a logarithmic function, and/or a combination thereof.

In some embodiments, the device 314 may include a second detector 424, which may be similar to the first detector 420 in that it may be any device capable of detecting electromagnetic radiation. Similar to the second detector 216 of FIG. 2, the second detector 424 of FIG. 4 may be used to detect radiating deviations stemming from the electromagnetic radiation source 404. Undesirable radiating deviations can occur in the intensity of the electromagnetic radiation 406 due to a wide variety of reasons and potentially causing various negative effects on the device 314. These negative effects can be particularly detrimental for measurements taken over a period of time. In some embodiments, radiating deviations can occur as a result of a build-up of film or material on the sampling window 412 which has the effect of reducing the amount and quality of light ultimately reaching the first detector 420. Without proper compensation, such radiating deviations could result in false readings and the output signal 320 would no longer be primarily or accurately related to the characteristic of interest.

To compensate for these types of undesirable effects, the second detector 424 may be configured to generate a compensating signal 426 generally indicative of the radiating deviations of the electromagnetic radiation source 404, and thereby normalize the output signal 320 generated by the first detector 420. As illustrated, the second detector 424 may be configured to receive a portion of the optically interacted radiation 414 via a beamsplitter 428 in order to detect the radiating deviations. In other embodiments, however, the second detector 424 may be arranged to receive electromagnetic radiation from any portion of the optical train in the device 314 in order to detect the radiating deviations, without departing from the scope of the disclosure.

As illustrated, the output signal 320 and the compensating signal 426 may be conveyed to or otherwise received by the signal processor 318 communicably coupled to both the detectors 420, 424. In one or more embodiments, the signal processor 318 may be configured to computationally combine the compensating signal 426 with the output signal 320 in order to normalize the output signal 320 in view of any radiating deviations detected by the second detector 424. In some embodiments, computationally combining the output and compensating signals 320, 426 may entail computing a ratio of the two signals 320, 426. For example, the concentration or magnitude of each characteristic of interest determined using the optical computing device 314 can be fed into an algorithm run by the signal processor 318. The algorithm may be configured to make predictions on how the characteristics of the substance 402 change if the concentration of the measured characteristic of interest changes.

In real-time or near real-time, the signal processor 318 may be configured to provide the resulting output signal 322 corresponding to the characteristic of interest in the substance 402. As briefly discussed above, the resulting signal output signal 322 may be conveyed, either wired or wirelessly, to an operator for analysis and consideration. In other embodiments, the resulting output signal 322 may be indicative of downloadable data configured to be downloaded to an external processing device at an appropriate time, such as when the mobile inline inspection device 308 is removed from the pipeline 302.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of monitoring a pipeline, comprising:
introducing a movable inline inspection device into the pipeline, the movable inline inspection device having a housing that defines a conduit therein which provides fluid communication through the movable inline inspection device in the form of a bypass fluid, the conduit having one or more optical computing devices arranged thereon for monitoring the bypass fluid, wherein each optical computing device has at least one integrated computational element arranged therein;
generating an output signal corresponding to a characteristic of the bypass fluid with at least one detector arranged within each optical computing device;
receiving the output signal from each optical computing device with a signal processor communicably coupled to the at least one detector of each optical computing device; and
determining with the signal processor the characteristic of the bypass fluid detected by each optical computing device.

2. The method of claim 1, wherein generating the output signal corresponding to the characteristic of the bypass fluid further comprises:
optically interacting electromagnetic radiation radiated from the bypass fluid flowing through the conduit with the at least one integrated computational element of each optical computing device;
generating optically interacted light from the at least one integrated computational element of each optical computing device; and
receiving with the at least one detector of each optical computing device the optically interacted light from the corresponding at least one integrated computational element.

3. The method of claim 1, further comprising:
emitting electromagnetic radiation from an electromagnetic radiation source arranged in each optical computing device;
optically interacting the electromagnetic radiation from each optical computing device with the bypass fluid; and
generating optically interacted radiation to be detected by the at least one detector in each optical computing device.

4. The method of claim 3, wherein the at least one detector in each optical computing device is a first detector, the method further comprising:
receiving and detecting with a second detector arranged in each optical computing device at least a portion of the electromagnetic radiation;
generating with each second detector a compensating signal indicative of radiating deviations of the corresponding electromagnetic radiation source;
computationally combining the output signal and the compensating signal of each optical computing device with the signal processor communicably coupled to the first and second detectors of each optical computing device; and
normalizing the output signal of each optical computing device.

5. The method of claim 1, further comprising providing with the signal processor a resulting output signal indicative of the characteristic of the bypass fluid.

6. The method of claim 1, wherein generating the output signal corresponding to the characteristic of the bypass fluid further comprises determining a concentration of a substance in the bypass fluid.

7. The method of claim 6, wherein the substance comprises a substance selected from the group consisting of barium, calcium, manganese, sulfur, sulfates iron, strontium, chlorine, paraffins, waxes, asphaltenes, aromatics, saturates foams, salts, dissolved mineral salts, particulates, sand, any combination thereof, and any derivatives thereof.

8. The method of claim 1, wherein generating the output signal corresponding to the characteristic of the bypass fluid further comprises determining a concentration of one or more reagents in the bypass fluid.

9. The method of claim 8, wherein the one or more reagents comprise a compound containing a substance selected from the group consisting of barium, calcium, manganese, sulfur, iron, strontium, and chlorine.

10. The method of claim 8, wherein the one or more reagents comprise a substance selected from the group consisting of paraffins, waxes, asphaltenes, aromatics, saturates, foams, and salts.

11. The method of claim 8, wherein the one or more reagents comprise a treatment reagent selected from the group consisting of acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers, lubricants, breakers, delayed release breakers, friction reducers, bridging agents, viscosifiers, weighting agents, solubilizers, rheology control agents, viscosity modifiers, pH control agents, hydrate inhibitors, relative permeability modifiers, diverting agents, consolidating agents, fibrous materials, bactericides, tracers, probes, and nanoparticles.

12. The method of claim 1, wherein generating the output signal corresponding to the characteristic of the bypass fluid further comprises determining a concentration of a product resulting from a chemical reaction occurring in the bypass fluid.

13. A method, comprising:
introducing a movable inline inspection device into a pipeline, the movable inline inspection device having a housing, a conduit defined within the housing to allow fluid communication through the housing, and one or more optical computing devices arranged on the conduit, wherein each optical computing device includes at least one integrated computational element;
flowing a bypass fluid through the conduit, wherein the one or more optical computing devices are in optical communication with the bypass fluid;
monitoring the bypass fluid with the one or more optical computing devices;
generating an output signal corresponding to a characteristic of the bypass fluid with at least one detector;
receiving the output signal from each optical computing device with a signal processor communicably coupled to the at least one detector; and
determining with the signal processor the characteristic of the bypass fluid detected by each optical computing device.

14. The method of claim 13, wherein flowing the bypass fluid through the conduit further comprises flowing a multiphase bypass fluid through the conduit.

15. The method of claim 13, wherein generating the output signal corresponding to the characteristic of the bypass fluid further comprises:
optically interacting electromagnetic radiation radiated from the bypass fluid flowing through the conduit with the at least one integrated computational element of each optical computing device;
generating optically interacted light from the at least one integrated computational element of each optical computing device; and
receiving with the at least one detector of each optical computing device the optically interacted light from the corresponding at least one integrated computational element.

16. The method of claim 13, further comprising:
emitting electromagnetic radiation from an electromagnetic radiation source arranged in each optical computing device;
optically interacting the electromagnetic radiation from each optical computing device with the bypass fluid; and
generating optically interacted radiation to be detected by the at least one detector in each optical computing device.

17. The method of claim 13, further comprising providing with the signal processor a resulting output signal indicative of the characteristic of the bypass fluid.

18. The method of claim 13, wherein generating the output signal corresponding to the characteristic of the bypass fluid further comprises determining a concentration of a substance in the bypass fluid, the substance being selected from the group consisting of barium, calcium, manganese, sulfur, sulfates iron, strontium, chlorine, paraffins, waxes, asphaltenes, aromatics, saturates foams, salts, dissolved mineral salts, particulates, sand, any combination thereof, and any derivatives thereof.

19. The method of claim 13, wherein generating the output signal corresponding to the characteristic of the bypass fluid further comprises determining a concentration of one or more reagents in the bypass fluid.

20. The method of claim 13, wherein generating the output signal corresponding to the characteristic of the bypass fluid further comprises determining a concentration of a product resulting from a chemical reaction occurring in the bypass fluid.

* * * * *